United States Patent [19]

Shum et al.

[11] Patent Number: 5,166,371

[45] Date of Patent: Nov. 24, 1992

[54] ASYMMETRIC EPOXIDATION USING A CHIRAL HYDROPEROXIDE

[75] Inventors: Wilfred P. Shum, West Chester; Haven S. Kesling, Jr., Drexel Hill; John G. Zajacek, Devon, all of Pa.

[73] Assignee: ARCO Chemical Technology, L.P., Wilmington, Del.

[21] Appl. No.: 743,001

[22] Filed: Aug. 9, 1991

Related U.S. Application Data

[63] Continuation of Ser. No. 386,655, Jul. 31, 1989, abandoned.

[51] Int. Cl.[5] .............................................. C07D 301/19
[52] U.S. Cl. ..................................... 549/529; 549/530
[58] Field of Search ................................ 549/529, 530

[56] References Cited

U.S. PATENT DOCUMENTS

| | | | |
|---|---|---|---|
| 3,351,635 | 11/1967 | Kollar | 549/529 |
| 3,983,143 | 9/1976 | Sheng et al. | 549/529 |
| 4,471,130 | 9/1984 | Katsuki et al. | 549/529 |

OTHER PUBLICATIONS

Pfenninger, "Synthesis", Feb. 1986, pp. 89–115.

*Primary Examiner*—C. Warren Ivy
*Assistant Examiner*—Ba K. Trinh
*Attorney, Agent, or Firm*—Stephen D. Harper

[57] ABSTRACT

Prochiral ethylenically unsaturated substrates are converted to chiral epoxides by reaction with optically active hydroperoxides in the presence of transition metal catalysts. For example, chiral glycidol is obtained by asymmetric epoxidation of allyl alcohol using optically active ethyl benzene hydroperoxide and a titaniuym alkoxide/tartrate catalyst. The chiral epoxide products are versatile synthetic intermediates.

31 Claims, No Drawings

ASYMMETRIC EPOXIDATION USING A CHIRAL HYDROPEROXIDE

This is a continuation of application Ser. No. 07/386,655, filed on Jul. 31, 1989, now abandoned.

BACKGROUND OF THE INVENTION

The present invention is directed to the asymmetric epoxidation of prochiral ethylenically unsaturated substrates. The epoxides obtained by the process of this invention are optically active and useful as synthetic intermediates in the preparation of a wide variety of physiologically active products. U.S. Pat. Nos. 4,471,130 and 4,764,628 teach to epoxidize allylic alcohols using racemic or achiral alkyl hydroperoxides and titanium complexes containing optically active alkoxide substituents as catalysts.

Rebek et al [*J. Org. Chem.* 43, 180(1978); *J. Am. Chem. Soc.* 102, 5602(1980)] disclose the epoxidation of olefins with optically active peroxy compounds derived from ketals, Schiff bases, or isoindolones. Only a low degree of asymmetric induction (<10% e.e) was observed.

Takata et al [*Bull. Chem. Soc. Jpn.* 59, 1275(1986); *Tetr. Lett.* 27, 1591(1986)] teach the asymmetric oxidation of sulfides with optically active peroxy compounds prepared by singlet oxygenation of thiazolidine derivatives. The optical purity of the sulfoxide products was moderate at best ($\leq 37\%$ e.e.).

It is clear that a need exists for alternative synthetic methods by which ethylenically unsaturated substrates may be epoxidized in an asymmetric manner to yield optically active products.

SUMMARY OF THE INVENTION

This invention provides a method for producing an optically active epoxide which comprises reacting a prochiral ethylenically unsaturated substrate with an optically active hydroperoxide in the presence of an effective amount of a catalyst selected from the group consisting of Group IV B, V B, or VI B transition metal compounds.

In one embodiment, the process comprises reacting a prochiral allylic alcohol with an optically active hydroperoxide of structure

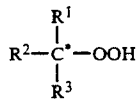

wherein $R^1$, $R^2$, and $R^3$ are different and are radicals selected from the group consisting of hydrogen, $C_1$–$C_{12}$ linear, branched, or cyclic alkyl, aralkyl, aryl, or substituted aryl. The reaction is performed in an inert solvent in the presence of an effective amount of a soluble transition metal catalyst selected from the group consisting of molybdenum, vanadium, titanium, zirconium, tantalum and tungsten compounds.

In another embodiment, the process of this invention comprises reacting allyl alcohol with optically active ethylbenzene hydroperoxide in an inert anhydrous organic solvent in the presence of an effective amount of a soluble titanium catalyst. Chiral glycidol is obtained as a product.

DETAILED DESCRIPTION OF THE INVENTION

Any suitable prochiral ethylenically unsaturated substrate may be asymmetrically epoxidized in accordance with the process of this invention. The term "prochiral" indicates that the substrate structure must make possible the formation of optically active epoxidized product. Symmetrically substituted ethylenically unsaturated substrates such as ethylene and tetramethylethylene thus are not suitable for use as substrates in this process since the corresponding epoxides will be achiral.

Examples of suitable ethylenically unsaturated substrates include, for example, substituted and unsubstituted aliphatic, alicyclic, and aromatic olefins which may be hydrocarbons, esters, alcohols, ketones, ethers, halides, or the like. The substrate may contain more than one carbon-carbon double bond and may be monomeric, oligomeric, or polymeric in nature. One class of preferred substrates are aliphatic and aromatic olefins having from 3 to 30 carbon atoms. Illustrative olefins are terminal or internal olefins such as propylene, 1-butene, 1-pentene, 2-pentene, 1-hexene, 2-hexene, 1-heptene, 2-heptene, 3-heptene, 1-octene, 2-octene, and 3-octene, aromatic vinyl compounds such as styrene, ar-substituted styrenes, and $\theta$-substituted styrenes, branched olefins such as 2-methyl-1-pentene and neohexene, and substituted cycloolefins such as 3-methyl-1-cyclohexene. Ethylenically unsaturated substrates having substituents containing halogen, oxygen, sulfur, or the like can be used, including, for example, allyl chloride, methallyl chloride, methyl methacrylate, methyl vinyl ketone, and the like.

More preferably, the process of this invention employs a substrate having an alcohol functionality (C—OH) and a carbon-carbon double bond wherein from 0 to 2 carbon atoms separate the alcohol functionality and the carbon-carbon double bond. Such substrates may be generally represented by the following formula:

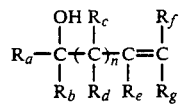

wherein n TM 0–2 and each R may be the same or different and may be any inert radical such as hydrogen, alkyl, aralkyl, aryl, substituted aryl or halide which does not interfere with the epoxidation.

The use of prochiral allylic alcohols (n TM 0) as substrates in the process of this invention is particularly preferred, although homoallylic alcohols are also suitable for use. Primary allylic alcohols of the following general structure are especially suitable:

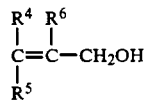

In such substrates, $R^4$, $R^5$, and $R^6$ are the same or different and may be radicals selected from the group consisting of hydrogen, $C_1$–$C_{12}$ linear or branched alkyl (methyl, ethyl, isopropyl, t-butyl, for instance), cycloalkyl (cyclohexyl, for example), aralkyl (such as benzyl), aryl (phenyl, napthyl, and the like), and substituted aryl (chlorophenyl or tolyl, for example). Illustrative allylic alcohols include allyl alcohol, methallyl alcohol, cinnamyl alcohol, crotyl alcohol, 2-cyclohexen-1-ol, 1-cyclohexen-1-methanol, 3-methyl-2-cyclohexen-1-ol, 2-phenyl-2-propen-1-ol, 2-cyclohexyl-2-propen-1-ol, 3-cyclohexyl-2-propen-1-ol, 2-penten-1-ol, geraniol, 1-cyclohexyl-2-propen-1-ol, 1-phenyl-2-propen-1-ol, 4-methoxy-2-buten-1-ol, 4-phenoxy-2-buten-1-ol, 2-hexen-1-ol, 2-decen-1-ol, 2,3-diphenyl-2-propen-1-ol,2,3-dimethyl-2-propen-1-ol, and the like and substituted derivatives thereof. Allyl alcohol is a preferred allylic alcohol since asymmetric epoxidation of this substrate will yield chiral glycidol, a useful synthetic intermediate in the preparation of optically active pharmaceuticals.

Another class of ethylenically unsaturated substrates useful in the process of this invention maybe represented by the general formula

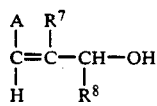

wherein A is a silyl group

a stannyl group

or a hologen (chloride, bromide, iodide, and the like) and $R^7$, and $R^8$, $R^9$, $R^{10}$, and $R^{11}$ are the same or different and are hydrogen, substituted or unsubstituted $C_1$–$C_{12}$ alkyl groups, substituted or unsubstituted aralkyl groups, or substituted or unsubstituted aryl groups. The optically active epoxy alcohols obtained from these substrates are versatile and useful intermediates for other optically active end-products by virtue of the reactivity of the A group, as described, for example, in EP No. 255,379.

In addition, any of the allylic or homoallylic alcohols which may be asymmetrically epoxidized by prior art processes, including, for example, epoxation using a racemic or achiral hydroperoxide and a titanium alkoxide/chiral ligand catalyst, can be used in the process of this invention. Examples of suitable allylic alcohols may be found in the following review articles: A. Pfenniner *Synthesis* 89 (1986); M. G. Finn, et al in *Asymmetric Synthesis* J. D. Morrison, Ed. Academic Press:New York, 1985, Vol. 5, Ch. 8, 247; B. E. Rossiter in *Asymmetric Synthesis* J. D. Morrison, Ed. Academic Press:New York, 1985, Vol. 5, Ch. 7, 193. The teachings of these papers are incorporated herein by reference in their entirety.

Any optically active hydroperoxide may be used in the process of this invention provided it possesses at least one chiral center. Preferably, the hydroperoxide is organic with the chiral center being the carbon bearing the hydroperoxy functionality. Hydroperoxides of this type thus can be secondary or tertiary and will have four different substituents attached to the hydroperoxy carbon. It is preferred that the three atoms directly attached to the hydroperoxy carbon, other than the oxygen of the hydroperoxy group, be carbon or hydrogen atoms. More preferably, the three substituents other than the hydroperoxy group are hydrogen or hydrocarbon substituents. Although generally it will be advantageous to employ a single optically active hydroperoxide, mixtures of optically active hydroperoxides may also be used. The optically active hydroperoxide may contain more than one hydroperoxy group. Since the degree of stereo selectivity during epoxidation is to some extent dependent on the optical purity of the hydroperoxide reagent, it is preferred to employ hydroperoxide in which one stereoisomer predominates. In general, the hydroperoxide should have an optical purity (as measured by enantiomeric excess) of at least about 10%. More preferably, the optical purity is at least about 50%. Most preferably, the enantiomeric excess of the optically active hydroperoxide is at least about 75%.

Preferred optically active hydroperoxides include those compounds corresponding to the general structure:

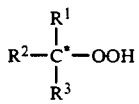

wherein $R^1$, $R^2$, and $R^3$ are different and are radicals selected from the group consisting of hydrogen, $C_1$–$C_{12}$ linear, branched, or cyclic alkyl, aralkyl, substituted aralkyl, aryl, or substituted aryl. In this structure, "*" indicates a chiral center. Illustrative radicals include methyl, ethyl, propyl, isopropyl, butyl, sec-butyl, iso-butyl, t-butyl, $C_5$–$C_{12}$ linear and branched aliphatic radicals, cyclohexyl, methyl cyclohexyl, cyclopentyl, benzyl, phenethyl, tolyl, naphthyl, phenyl, halophenyl, and the like. The radicals may contain elements other than carbon and hydrogen such as oxygen, halogen, and sulfur, provided these other elements or functional groups do not interfere with the desired asymmetric epoxidation. Particularly preferred optically active hydroperoxides are those where $R_1$ is hydrogen or methyl, $R^2$ is methyl or ethyl, and $R^3$ is phenyl, naphthyl, or propyl, provided each R group is different. Illustrative examples of such hydroperoxides include ethyl benzene hydroperoxide ($R^1$ TM H, $R^2$ TM methyl, $R^3$ TM phenyl), ethyl naphthalene hydroperoxide ($R^1$ TM H, $R^2$ TM methyl, $R^3$ TM naphthyl), propyl benzene hydroperoxide ($R^1$ TM H, $R^2$ TM ethyl, $R^3$ TM phenyl), 2-hydroperoxy pentane ($R^1$ TM H, $R^2$ TM methyl, $R^3$ TM propyl), 2-hydroxy-2-phenyl butane ($R^1$ TM methyl, $R^2$ TM ethyl, $R^3$ TM phenyl), and 3-hydroperoxy-3-methyl hexane ($R^1$ TM methyl, $R^2$ TM ethyl, $R^3$ TM propyl). Ethylbenzene hydroperoxide, which may be prepared by oxidation of ethylbenzene or by any other of the methods known in the art, is the preferred hydroperoxide because of its low cost and availability.

Any suitable method may be used to obtain the optically active hydroperoxide. A number of such methods have been described in the art, including enzymatic resolution of racemic hydroperoxides [N. Baba, et al *Agric. Biol. Chem.* 52. 2685 (1988)], singlet oxygenation of thiazolidine derivatives [T. Takata, et al *Bull. Chem. Soc. Jpn.* 59, 1275(1986)], perhydrolysis of optically active ketals, Schiff's bases, or isoindolones [J. Rebek, Jr., et al *J. Am. Chem. Soc.* 102, 5602 (1980)], liquid chromatographic resolution and subsequent hydrolysis of perketals [P. Dussault, et al *J. Am. Chem. Soc.* 110, 6276(1988)], oxidation of optically active 1-phenylethanol [A. G. Davies, et al *J. Chem. Soc.* 665(1956); *J. Chem. Soc. (B)*, 17(1967)]and oxidation of optically active halides with platinum dioxy9en complexes Y. Tatsuno et al *J. Am. Chem. Soc.* 103, 5832(1981)].

Any metallic compound capable of catalyzing the epoxidation of an ethylenically unsaturated substrate with a hydroperoxide can be used in the process of this invention. Suitable catalysts include compounds of the Group IV B, V B, and VI B transition metals, particularly molybdenum, vanadium, titanium, zirconium, tantalum and tungsten compounds. The catalyst may be employed in the asymmetric epoxidation reaction in the form of a compound or mixture of compounds which is initially soluble in the reaction medium. However, heterogeneous catalysts are also suitable for use in this process. Suitable transition metal catalysts are described in R. A. Sheldon *Aspects Homogeneous Catal.* 4, 3(1981) and K. A. Jorgensen *Chem. Rev.* 89, 431(1989).

The metallic compounds useful as catalysts may contain a variety of substituents and ligands. The selection of particular substituents or ligands will depend on the desired activity and solubility of the catalyst. Without wishing to be bound by theory, it is believed that under certain reaction conditions the initially added catalyst may be converted into a different catalytically active species by interaction with the ethylenically unsaturated substrate, the optically active hydroperoxide, or other compounds present in the epoxidation reaction mixture. Illustrative forms of the catalysts include naphthenates, stearates, octoates, carbonyls, alkoxides, glycolates, oxides, halides, phosphates, sulfates, carbamates, thioarbamates, acetylacetonates, cyclopentadienyl compounds, nitrites, nitrates, borates, carbonates, formates, acetates, phosphinates, propionates, oxalates, phthalates, sulfonates, phenoxides, aminates, amidates, borates, borides, cyanides, tropolonates, hydroxides, alkylates, arylates, ammoniates, carboxylates and the like. The catalysts may contain more than one type of metal and may also be compounds having more than one metal center (e.g., a heteropolyacid or a compound existing in dimeric or polymeric form).

Examples of suitable catalysts include, but are not limited to, titanium n-butoxide, titanium methoxide, titanium diisopropoxide bis(acetylacetonate), titanium stearylate, titanium ethoxide, titanium oxide bis(acetylacetonate), titanium isopropoxide, titanium propoxide, titanium cresylate, titanium 2-ethylhexoxide, titanium isobutoxide, zirconium acetylacetonate, zirconium n-butoxide n-butyl alcohol complex, zirconium ethoxide, zirconium isopropoxide, zirconium pentoxide, zirconium propoxide, vanadium acetylacetonate, vanadium naphthenate, vanadyl acetylacetonate, vanadyl isopropoxide, vanadyl propoxide, niobium ethoxide, niobium butoxide, niobium phenoxide, tantalum ethoxide, tantalum methoxide, molybdenum hexacarbonyl, molybdenum oxide bis(acetylacetonate), molybdenum acetate dimer, molybdenum thiocarbamate, tungsten hexacarbonyl, molybdenum oxide dioxinate, molybdenum naphthenate, polyorganotitananosiloxanes, tungsten naphthenate, niobium naphthenate, tantalum naphthenate, niobium boride, molybdenum boride, zirconium boride, tungsten boride, vanadium boride, molybdenum oxide bis(oxine) and the like and mixtures thereof.

Catalyst solutions useful in the process of this invention may be prepared by any of the methods known in the art for producing soluble transition metal epoxidation catalysts. Such methods include, for example, reacting molybdenum, vanadium, or tungsten metal or a difficultly soluble derivative such as a sulphide, ammoniate, halide, oxide, hydroxide, oxyhalide, phosphate, or the like with an organic hydroperoxide, monohydric alcohol, dialkylene glycol, polyhydric compound, monocarboxylic acid, dicarboxylic acid, silicon or phosphorus compound, organic amine, or some combination thereof. Exemplary methods are described in U.S. Pat. Nos. 3,507,809; 3,573,226; 3,362,972; 3,480,563; 3,453,218; 3,434,975; 4,607,113; 4,687,868; 4,772,731; 3,578,690; 3,784,482; 3,856,826; 3,856,827; 3,787,329; 4,590,172; and 4,593,012, the teachings of which are incorporated herein by reference.

Any heterogeneous, supported, or polymer-bound transition metal epoxidation catalyst may be used in the process of this invention. Exemplary catalysts of this typ include poly(vinyl aromatic) resins containing chelated vanadium or molybdenum [T. Yokoyama et al *Bull. Chem Soc. Jpn.* 58, 3271(1985); K. Zhang et al *J. Polym. Sci., Polym Chem. Ed.* 23, 1213(1985); E. C. Chapman et al *J. Appl. Polym. Sci.* 27, 811(1982); S. Bhaduri et al *J. Chem. Soc., Dalton Trans.* 447(1981)], silica-supported molybdenum, titanium, zirconium, or vanadium [U.S. Pat. Nos. 3,634,464; 3,829,392; 3,923,843; 4,021,454; 4,367,342], molybdenum zeolites M. B. Ward et al *J. Mol. Cat.* 27, 1(1987), cationic exchange resins containing molybdenum or vanadium R. Boeva et al *React. Kinet. Catal. Lett.* 24, 239(1984); G. L. Linden et al *Inorg. Chem.* 16, 3170(1977)], and polymer-bound zirconocene and hafnocene chlorides [B.-H. Chang et al *J. Orgamomet. Chem.* 280, 365(1985)].

The use of a soluble transition metal alkoxide catalyst having a coordination number of at least four is preferred in the process of this invention. Such catalysts include those having the following general unit formula:

$M(OR)_n$ wherein M is titanium, zirconium, or tantalum, R is a $C_1$-$C_{12}$ linear or branched alkyl radical and n=4 or 5. Soluble titanium alkoxide catalysts are preferred; the alkoxide substituents may be derived from the monohydric or polyhydric alcohols.

Examples of suitable alkoxide substituents include methoxide, ethoxide, propoxide, isopropoxide, n-butoxide, t-butoxide, isobutoxide, and the like. Suitable catalysts may also be obtained by reacting a metal alkoxide of formula $M(OR)_n$ above with a diol. Preferably, the diol has the following general structure:

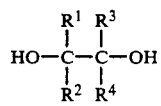

wherein $R^1$, $R^2$, $R^3$, and $R^4$ are the same or different and are radicals selected from the group consisting of hydrogen, carboxylate

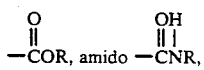

$C_1$–$C_{12}$ linear, branched, or cyclic alkyl, aralkyl, aryl, and substituted aryl radicals. Alternatively, such catalysts may be obtained by reacting transition metal halide derivatives with diols or alkali metal salts of diols. The catalysts obtained by either method may be monomeric or polymeric (e.g., dimeric) in structure, depending on the metal and the structure and number of substituents. Preferably, the molar ratio of diol to transition metal is from about 0.9 to 2. Illustrative diols include propylene glycol, 2,3-butanediol, 3,4-dimethyl-3,4-hexanediol, 4,5-octanediol, 2,3-hexanediol, 1,3-di(p-nitrophenyl)propane-1,2-diol, 2,4-pentanediol, dimethyl tartrate, diisopropyl tartrate, distearyl tartrate, diphenyl tartrate, dibenzyl tartramide, dibutyl tartramide, dicyclohexyl tartramide, tartaric acid diamide, N,N-dimethyl tartaric acid diamide, 1,2-cyclopentanediol, 1,2-cyclohexanediol-1,2-dicarboxylate, dimethyl 2,4-dihydroxyglutarate, ethyl N,N-diethyl tartrate monoamide, 2,5-dioxo-3,4-octanediol, 1,2-bis-acetylethylene glycol, bis-2,2'-(2-hydroxycaprolactone), and the like and mixtures thereof. Amino alcohols or diamines may also be combined with metal alkoxides to yield suitable catalysts. Illustrative examples of such amino alcohols and diamines include 2-amino-1-propanol, 2-amino-1-butanol, 2-amino-3-methyl-1-butanol, 2-amino-3-phenyl-1-propanol, 2-pyrrolidine methanol, ephedrine, and the like and mixtures thereof. Derivatives of hydroxamic acid, pyridine dimethanol and pyridine methanol are also useful metal catalyst substituents. In contrast to prior art methods, it is not necessary for any of the substituents on the metal catalyst to be optically active.

The process of this invention is preferably carried out in a liquid medium, preferably an inert organic solvent in which all of the reaction components are soluble. Preferred organic solvents include halogenated hydrocarbons such as methylene chloride and carbon tetrachloride, aromatic hydrocarbons such as toluene and benzene, and aliphatic hydrocarbons such as heptane and isooctane It is preferred that the reaction medium be anhydrous; the use of a dessicant such as molecular sieves can be advantageous. Although not critical, the asymmetric epoxidation is preferably carried out under an inert atmospheric (nitrogen or argon for example).

The reaction temperature and time required will vary from about 1 minute to 7 days at from about −100° C. to 150° C., depending on the catalyst, ethylenically unsaturated substrate, and optically active hydroperoxide used. For titanium alkoxide catalysts and allylic alcohol substrates, for example, mild conditions are generally suitable using a hydroperoxide such as ethyl benzene hydroperoxide. Using reagents of this type, reaction temperatures between about -100° C. and 80° C., or, more preferably, between about −50° C. to 30° C. are normally effective. Typical reaction times under such conditions are from as little as 5 minutes to 24 hours. The time is not critical and can readily be optimized for a particular set of conditions and reactants. In any event, the reaction time and temperature should be sufficient to accomplish asymmetric epoxidation of the ethylenically unsaturated substrate.

The manner in which the reactants are combined is not critical, but generally slow addition of the optically active hydroperoxide to a stirred solution of catalyst and ethylenically unsaturated substrate will be preferred.

The amount of catalyst used relative to the amount of substrate may be varied widely, depending on the substrate structure, the reaction conditions, the activity of the catalyst, and the rate of reaction desired, among other factors. The catalyst concentration should be sufficient to effect asymmetric epoxidation of the substrate. Normally, the molar ratio of catalyst to substrate is preferred to be from about 1:200 to 1:1. The hydroperoxide is generally added in at least stoichrometric amounts relative to substrate and preferably in excess. For reasons of economy, the molar ratio of hydroperoxide to substrate is preferably not greater than about 3:1.

After epoxidation has been completed to the desired degree, the optically active epoxide may be separated from the reaction medium by any suitable means. Such methods will be apparent to those skilled in the art and generally will be analogous to the procedures employed for the recovery of epoxides prepared by other epoxidation processes. Where the epoxide product is water-insoluble, recovery can be effected by isolation and fractional distillation of the resulting organic layer. Epoxide products which are crystalline solids at room temperature may be purified by recrystallization from an appropriate solvent. If the optically active epoxide is water-soluble (e.g., glycidol), salting out, extraction or chromatography may be used. Suitable purification procedures are described in more detail in the references noted in A. Pfenninger *Synthesis* 89(1986) and Y. Gao, et al *J. Am. Chem. Soc.* 109, 5765(1987). Alternatively, the optically active epoxide is not isolated but reacted in situ to form useful derivatives (see Gao, et al, for illustrative examples).

Without further elaboration, it is believed that one skilled in the art can, using the preceding description, utilize the present invention to its fullest extent. The following examples, therefore, are to be considered as merely illustrative and not limitative of the claims or remainder of the disclosure in any way whatsoever.

EXAMPLE 1

To prepare optically active ethyl benzene hydroperoxide, the procedure described by Baba et al [*Agric. Biol. Chem.* 52, 2688 (1988)]was generally followed. A solution containing 50 g racemic ethyl benzene hydroperoxide (90% purity), 25 g isopropenyl acetate, 1750 mL cyclohexane, and 150 g Amano P lipase (a lipoprotein lipase from Pseudomonas fluorescens) was stirred at 25° C. for 48 hours. Conversion of hydroperoxide was determined to be 38% by iodometric titration. The lipase enzyme was removed by filtration and the filtrate washed twice with 400 mL water to remove the acetic acid formed. The organic fraction was concentrated and then purified by column chromatography (95% minimum ethyl benzene hydroperoxide purity; 22 g yield). The resolved s(−)-ethyl benzene hydroperoxide thus obtained exhibited an optical rotation of −52°, corresponding to an e.e. (enantiomeric excess) of about 50%.

The following example illustrates asymmetric epoxidation of an ethylenically unsaturated substrate in accordance with the process of this invention. A solution containing 4.1 g (72 mmol) allyl alcohol, 1.01 g (4.3 mmol) racemic diisopropyl tartrate, 1.01 g (3.6 mmol) titanium isopropoxide, 2 g 4A molecular sieves, and 180 mL methylene chloride was stirred under argon at −20° C. for 15 minutes. To this solution was added dropwise with stirring 21 g (152 mmol) of the resolved S(−)-ethyl benzene hydroperoxide. The mixture was kept at −20° C. until a 30% glycidol yield was obtained as measured by GLC analysis. The glycidol was recovered by extracting with 30 mL water, and then purified by fractional distillation after removing the water at reduced pressure.

To determine optical purity, the isolated glycidol was reacted with R(+)-2-methoxy-2-(trifluoromethyl) phenyl acetyl chloride to form the glycidyl Mosher ester. It wa found by $^{13}$C NMR analysis that R(+)-glycidol was the major isomer present with an e.e. of 43%.

EXAMPLES 2-13

In these examples, the asymmetric epoxidation of a number of different allylic alcohols is conducted by charging into a suitable reaction vessel 100 parts by weight of a substrate corresponding to the general formula

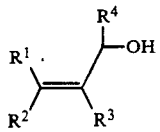

together with 400 parts by weight of solvent and the amounts of transition metal catalyst and optically active hydroperoxide given in Table I. The optically active hydroperoxides are prepared by the procedure of Baba et al [*Agric. Biol. Chem.* 52, 2688(1988)]. The reaction mixture is heated or cooled with agitation at the stated temperature for the indicated period of time under a nitrogen atmosphere. The chiral epoxyalcohol products which are water-soluble are isolated following the work-up procedure of Example 1. The water-insoluble chiral epoxyalcohol products are purified by fractional distillation of the crude reaction mixture (including prior neutralization or removal of the catalyst or excess unreacted hydroperoxide if the epoxyalcohol is relatively unstable) or by recrystallization from an appropriate solvent.

EXAMPLES 14-16

The asymmetric epoxidation of homoallylic alcohols of structure

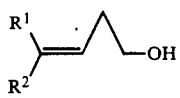

is conducted by charging into a suitable vessel 100 parts by weight of the substrate, 200 parts by weight of methylene chloride, and the amount of transition metal catalyst stated in Table II. The molar ratio of optically active hydroperoxide to substrate in each example is 1.5. The reaction mixture is heated or cooled with agitation at the stated temperature for the indicated period of time under a nitrogen atmosphere. The chiral epoxide products are separated from the crude reaction mixture by the procedures described in Examples 1-13.

TABLE I

| EXAMPLE NO. | $R^1$ | $R^2$ | $R^3$ | $R^4$ | CATALYST | gCAT/MOLE SUBSTRATE |
|---|---|---|---|---|---|---|
| 2 | H | H | Me | H | VO(acac)$_2$ | 0.2 |
| 3 | Benzyl | H | H | H | MoO$_2$(acac)$_2$ | 0.2 |
| 4 | H | n-C$_{10}$H$_{21}$ | H | H | $a$ | 2.5$^m$ |
| 5 | H | H | Cyclohexyl | H | Mo(CO)$_6$ | 0.34 |
| 6 | Ph | H | H | H | Ta Naphthenate$^b$ | 0.33 |
| 7 | H | (CH$_2$)$_4$ | | H | $c$ | 6.6 |
| 8 | H | PhCH$_2$OCH$_2$— | H | H | MoO$_3$ + DPG$^d$ | 0.08 |
| 9 | H | H | H | Et | WB | 2.7 |
| 10 | Et | H | Me | H | Cp$_2$Ti(OC$_6$H$_5$)$_2$$^n$ | 0.3 |
| 11 | H | Me | H | Cyclohexyl | $e$ | 14$^m$ |
| 12 | H | H | Me | Et | $f$ | 16$^m$ |
| 13 | H | —Si(CH$_3$)$_3$ | H | —(CH$_2$)$_3$CO$_2$Me | $g$ | 12$^m$ |

| EXAMPLE NO. | TEMP., °C. | TIME HR | HYDROPEROXIDE | MOLES HYDROPEROXIDE/ MOLES SUBSTRATE | SOLVENT |
|---|---|---|---|---|---|
| 2 | 80 | 4 | EBHP$^h$ | 1.1 | benzene |
| 3 | 80 | 3 | ENHP$^i$ | 1.5 | toluene |
| 4 | 25 | 6 | HPP$^j$ | 2.0 | isooctane |
| 5 | 80 | 1.5 | HPPB$^k$ | 2.0 | isooctane |
| 6 | 70 | 1 | EBHP | 1.3 | benzene |
| 7 | 100 | 1 | EBHP | 2.0 | ethyl benzene |
| 8 | 120 | 4 | HPMH$^l$ | 2.0 | benzene |
| 9 | 110 | 7 | HPPB | 2.0 | benzene |
| 10 | 25 | 6 | EBHP | 2.0 | ethyl benzene |
| 11 | −20 | 72 | EBHP | 2.0 | CH$_2$Cl$_2$ |
| 12 | −20 | 72 | EBHP | 1.5 | CH$_2$Cl$_2$ |

TABLE I-continued

| | | | | | | |
|---|---|---|---|---|---|---|
| 13 | 0 | 24 | EBHP | | 2.5 | $CH_2Cl_2$ |

Notes:
[a] $VO(acac)_2$ + N-benzoyl-N-phenylhydroxylamine; prepared by the procedure of J. Am.-Chem. Soc. 99, 1990(1977).
[b] containing 9.4 wt. % tantalum
[c] silylated titanium on silica, prepared according to Example 1 of U.S. Pat. No. 3,829,392
[d] reaction product of molybdenum trioxide and dipropylene glycol, prepared in accordance with Example 1 of U.S. Pat. No. 4,687,868 (containing 150 ppm Mo)
[e] $Ti(OnBu)_4$ + dibutyl tartramide (1:1)
[f] $Ta(OEt)_5$ + diethyl tartrate (1:1)
[g] $Ti(OiPr)_4$ + 2-amino-1-propanol (1:1)
[h] ethyl benzene hydroperoxide
[i] ethyl naphthalene hydroperoxide
[j] 2-hydroperoxy pentane
[k] 2-hydroperoxy-2-phenyl butane
[l] 3-hydroperoxy-3-methyl hexane
[m] based on weight of metal alkoxide or complex employed
[n] prepared by the procedure of K. Andra J. Organomet. Chem. 11, 567(1968)

TABLE II

| EXAMPLE NO. | $R^1$ | $R^2$ | CATALYST | gCAT/MOLE SUBSTRATE | TEMP., °C. | TIME HR | HYDROPEROXIDE |
|---|---|---|---|---|---|---|---|
| 14 | Pr | H | a | 15[c] | 0 | 72 | EBHP[d] |
| 15 | H | H | b | 10[c] | −20 | 18 | ENHP[e] |
| 16 | Ph | Et | $Ti(OiPr)_2(acac)_2$ | 3 | 25 | 24 | HPP[f] |

[a] $Zr(OPr)_4$ + dicyclohexyl tartramide; prepared in accordance with the procedure of S. Ikegam et al Chem. Lett. 83(1987)
[b] $Ti(OiPr)_4$ + diethyl tartrate; prepared by the procedure of U.S. Pat. No. 4,471,130
[c] based on weight of metal alkoxide
[d] ethyl benzene hydroperoxide
[e] ethyl naphthalene hydroperoxide
[f] 2-hydroperoxy-2-phenyl butane

We claim:

1. A method for producing an optically active epoxide which comprises reacting a prochiral ethylenically unsaturated substrate with an optically active hydroperoxide having an optical purity as measured by enantiomeric excess of at least about 10% in the presence of an effective amount of an optically inactive catalyst selected from the group consisting of Group IV B, V B, or VI B transition metal compounds.

2. The method of claim 1 wherein the prochiral ethylenically unsaturated substrate is a substrate having an alcohol functionality and a carbon-carbon double bond wherein from 0 to 2 carbon atoms separate the alcohol functionality and the carbon-carbon double bond.

3. The method of claim 1 wherein the prochiral ethylenically unsaturated substrate is an allylic alcohol.

4. The method of claim 1 wherein the prochiral ethylenically unsaturated substrate is an allylic alcohol of general structure

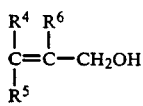

wherein $R^4$, $R^5$, and $R^6$ are the same or different and are radicals selected from the group consisting of hydrogen, $C_1$–$C_{12}$ linear or branched alkyl, cycloalkyl, aralkyl, aryl, and substituted aryl.

5. The method of claim 1 wherein the optically active hydroperoxide has the general structure

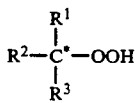

wherein $R^1$, $R^2$, and $R^3$ are different and are radicals selected from the group consisting of hydrogen, $C_1$–$C_{12}$ linear, branched, or cyclic alkyl, aralkyl, substituted aralkyl, aryl, and substituted aryl.

6. The method o claim 1 wherein the optically active hydroperoxide is ethyl benzene hydroperoxide.

7. The method of claim 1 wherein the reaction is carried out in an inert organic solvent.

8. The method of claim 1 wherein the optically inactive catalyst is a transition metal compound selected from the group consisting of molybdenum, vanadium, titanium, tantalum, zirconium, and tungsten compounds.

9. The method of claim 1 wherein the optically inactive catalyst is a soluble transition metal alkoxide catalyst of formula $M(OR)_n$ wherein M is titanium, zirconium, or tantalum, R is an optically inactive $C_1$–$C_{12}$ linear branched alkyl radical, and n TM 4 or 5.

10. The method of claim 1 wherein the optically inactive catalyst is obtained by reacting a metal alkoxide of formula $$M(OR)_n$$

wherein M is titanium, zirconium, or tantalum, R is a $C_1$–$C_{12}$ linear or branched alkyl radical, and n TM 4 or 5, with an optically inactive diol of structure

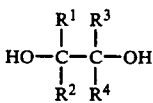

wherein $R^1$, $R^2$, and $R^4$ are the same or different and are radicals selected from the group consisting of hydrogen, carboxylate, amido, $C_1$–$C_{12}$ linear, branched, or cyclic alkyl, aralkyl, aryl, and substituted aryl radicals such that the diol is optically inactive.

11. The method of claim 1 wherein the mole ratio of prochiral ethylenically unsaturated substrate to optically active hydroperoxide is from about 1:1 to 1:3.

12. The method of claim 1 wherein the mole ratio of the optically inactive catalyst to the prochiral ethylenically unsaturated substrate is from about 1:200 to 1:1.

13. A method for producing an optically active epoxy alcohol which comprises reacting a prochiral allylic alcohol with an optically active hydroperoxide having an optical purity as measured by enantiomeric excess of at least about 25% and a structure

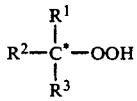

wherein $R^1$, $R^2$, and $R^3$ are different and are radicals selected from the group consisting of hydrogen, $C_1$-$C_{12}$ linear, branched, or cyclic alkyl, aralkyl, substituted aralkyl, aryl, or substituted aryl, said reaction being performed in an inert organic solvent in the presence of an effective amount of a soluble optically inactive transition metal catalyst selected from the group consisting of molybdenum, vanadium, titanium, tantalum, zirconium, and tungsten compounds.

14. The method of claim 13 wherein the prochiral allylic alcohol has the general structure

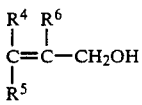

wherein $r^4$, $R^5$, and $R^6$ are the same or different and are radicals selected from the group consisting of hydrogen, $C_1$-$C_{12}$ linear or branched alkyl, cycloalkyl, aralkyl, aryl, and substituted aryl.

15. The method of claim 13 wherein the prochiral allylic alcohol is allyl alcohol or methallyl alcohol.

16. The method of claim 13 wherein $R^1$ is hydrogen or methyl, $R^2$ is methyl or ethyl, $R^3$ is phenyl, naphthyl, or propyl, and $R^1$, $R^2$, and $R^3$ are different.

17. The method of claim 13 wherein the optically active hydroperoxide is ethyl benzene hydroperoxide.

18. The method of claim 13 wherein the reaction is carried out under anhydrous conditions.

19. The method of claim 13 wherein the catalyst is a soluble optically inactive transition metal alkoxide catalyst of formula

wherein M is titanium, zirconium, or tantalum, R is an optically inactive $C_1$-$C_{12}$ linear or branched alkyl radical, and n=4 or 5.

20. The method of claim 13 wherein the optically inactive transition metal catalyst is obtained by reacting a metal alkoxide of formula

wherein M is titanium, zirconium, or tantalum, R is a $C_1$-$C_{12}$ linear or branched alkyl radical, and n=4 or 5, with an optically inactive diol of structure

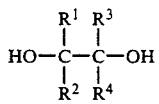

wherein $R^1$, $R^2$, $R^3$, and $R^4$ are the same or different and are radicals selected from the group consisting of hydrogen, carboxylate, amido, $C_1$-$C_{12}$ linear, branched, or cyclic alkyl, aralkyl, aryl, and substituted aryl radicals such that the diol is optically inactive.

21. The method of claim 13 wherein the molar ratio of prochiral allylic alcohol to optically active hydroperoxide is from about 1:1 to 1:3.

22. The method of claim 13 wherein the molar ratio of soluble optically inactive transition metal catalyst to prochial allylic alcohol is from about 1:200 to 1:.

23. The method of claim 13 comprising the additional step of separating the optically active epoxy alcohol from the inert organic solvent.

24. The method of claim 13 wherein the reaction is conducted at a temperature of from about −100° C. to 150° C.

25. A method for producing optically active glycidol which comprises reacting allyl alcohol with optically active ethyl benzene hydroperoxide having an optical purity as measured by enantiomeric excess of at least about 50% in an inert anhydrous organic solvent in the presence of an effective amount of a soluble optically inactive titanium catalyst.

26. The method of claim 25 wherein the soluble optically inactive titanium catalyst has the general unit formula

wherein R is a $C_1$-$C_{12}$ linear or branched optically inactive alkyl radical.

27. The method of claim 25 wherein the soluble optically inactive titanium catalyst is obtained by reacting a compound of formula

wherein R is a $C_1$-$C_{12}$ linear or branched alkyl radical with an optically inactive diol of structure

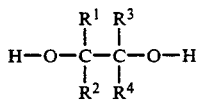

wherein $R^1$, $R^2$, $R^3$, and $R^4$ are the same or different and are radicals selected from the group consisting of hydrogen, carboxylate, amidoc, $C_1$-$C_{12}$ linear, branched, or cyclic alkyl, aralkyl, aryl, and substituted aryl radicals such that the diol is optically inactive.

28. The method of claim 25 wherein the molar ratio of allyl alcohol to optically active ethyl benzene hydroperoxide is from about 1:1 to 1:3.

29. The method of claim 25 wherein the molar ratio of soluble optically inactive titanium catalyst to allyl alcohol is from about 1:200 to 1:1.

30. The method of claim 25 comprising the additional step of separating the optically active glycidol from the inert anhydrous organic solvent.

31. The method of claim 25 wherein the reaction is conducted at a temperature of from about −50° C. to 30° C.

* * * * *